United States Patent [19]
Glenn, Jr.

[11] Patent Number: 5,854,293
[45] Date of Patent: Dec. 29, 1998

[54] LIQUID PERSONAL CLEANSING COMPOSITION WHICH CONTAIN A LIPOPHILIC SKIN MOISTURIZING AGENT COMPRISED OF RELATIVELY LARGE DROPLETS

[75] Inventor: Robert Wayne Glenn, Jr., Maineville, Ohio

[73] Assignee: The Procter & Gamble Company, Cincinnati, Ohio

[21] Appl. No.: 717,379

[22] Filed: Sep. 23, 1996

[51] Int. Cl.$^6$ ................................................ A61K 7/035
[52] U.S. Cl. ........................ 514/844; 424/69; 424/70.1; 424/70.19; 424/70.22; 424/78.02; 514/846; 514/847
[58] Field of Search ..................... 514/844, 846, 514/847; 424/69, 70.1, 70.19, 70.22, 78.02

[56] References Cited

U.S. PATENT DOCUMENTS

| | | | |
|---|---|---|---|
| 3,829,563 | 8/1974 | Barry et al. | 424/70 |
| 4,840,746 | 6/1989 | Shiozaki et al. | 252/174.25 |
| 5,043,161 | 8/1991 | Scarpelli et al. | 424/401 |
| 5,154,849 | 10/1992 | Visscher et al. | 252/174.15 |
| 5,308,526 | 5/1994 | Dias et al. | 252/125 |
| 5,312,559 | 5/1994 | Kacher et al. | 252/125 |
| 5,439,682 | 8/1995 | Wivell et al. | 724/401 |
| 5,441,730 | 8/1995 | Gough et al. | 424/70.11 |
| 5,456,863 | 10/1995 | Bergmann | 252/547 |

FOREIGN PATENT DOCUMENTS

| | | | |
|---|---|---|---|
| 258707 | 3/1988 | European Pat. Off. | |
| 316054 | 5/1989 | European Pat. Off. | |
| 0 452202 A1 | 10/1991 | European Pat. Off. | A61K 7/00 |
| 0 738509 A2 | 10/1996 | European Pat. Off. | A61K 7/48 |
| 03034914 | 6/1989 | Japan. | |
| 05310539 | 5/1992 | Japan. | |
| 05310540 | 5/1992 | Japan. | |
| 684784 | 7/1967 | South Africa. | |
| 2125428 | 3/1984 | United Kingdom. | |
| WO 96/02224A1 | 2/1996 | WIPO | A61K 7/00 |
| WO 96/02225 | 2/1996 | WIPO | A61K 7/00 |
| WO 96/02229 | 2/1996 | WIPO. | |
| WO 96/17592 | 6/1996 | WIPO. | |
| WO 96/25144 | 8/1996 | WIPO | A61K 7/48 |
| WO 96/29979 | 10/1996 | WIPO | A61K 7/50 |
| WO 97/32568 | 9/1997 | WIPO | A61K 7/50 |

*Primary Examiner*—Terressa Mosley
*Attorney, Agent, or Firm*—Darryl C. Little; Tara M. Rosnell; George W. Allen

[57] ABSTRACT

Moisturizing liquid personal cleansing emulsion compositions which comprise a moisturizing phase and an aqueous cleansing phase are disclosed. The moisturizing phase comprises from about 1% to about 35% by weight of the composition of lipophilic skin moisturizing agents comprised of droplets having a particle size distribution such that at least about 10% by weight of the droplets have a diameter of at least about 500 microns. The aqueous cleansing phase comprises from about 0.1% to about 10% by weight of the composition of a stabilizer, from about 5% to about 30% by weight of the composition of a lathering surfactant, and water.

17 Claims, No Drawings

LIQUID PERSONAL CLEANSING COMPOSITION WHICH CONTAIN A LIPOPHILIC SKIN MOISTURIZING AGENT COMPRISED OF RELATIVELY LARGE DROPLETS

TECHNICAL FIELD

The present invention relates to liquid personal cleansing compositions which provide clinically efficacious moisturization to the skin. The liquid personal cleansing compositions of the present invention are emulsions which contain a moisturizing phase comprising a lipophilic skin moisturizing agent and an aqueous cleansing phase comprising a surfactant and a stabilizer. The lipophilic moisturizing agents which comprise the liquid personal cleansing compositions herein themselves comprise droplets which have a particle size distribution such that at least about 10% by weight of the droplets are greater than about 500 microns in diameter.

BACKGROUND OF THE INVENTION

Liquid personal cleansing products are becoming more popular in the United States and around the world. Desirable liquid personal cleansing compositions must meet a number of criteria. For example, in order to be acceptable to consumers, a liquid personal cleansing product must exhibit good cleaning properties, must exhibit good lathering characteristics, must be mild to the skin (not cause drying or irritation) and preferably should even provide a moisturization benefit to the skin.

Liquid personal cleansing products which contain high levels of lipophilic skin conditioning agents have been disclosed. In fact, consumer products, such as Olay Moisturizing Body Wash, which, especially when used with the Olay Cleansing Puff, deposit lipophilic skin conditioning agents on the skin are enormously popular with consumers. Nevertheless, some consumers would prefer to have an even greater moisturizing benefit delivered from these liquid personal cleansing products. Therefore, it would be desirable to provide a liquid personal cleansing composition with even greater moisturizing properties.

It has now been found that the deposition of a lipophilic skin moisturizing agent on the skin can be dramatically increased if the lipophilic skin moisturizing agent comprises relatively large oil droplets.

SUMMARY OF THE INVENTION

The present invention relates to liquid personal cleansing emulsion compositions which comprise a moisturizing phase and an aqueous cleansing phase. The moisturizing phase comprises from about 1% to about 30% by weight of the composition of lipophilic skin moisturizing agents comprised of droplets having a particle size distribution such that at least about 10% by weight of the droplets have a diameter of at least about 500 microns. The aqueous cleansing phase comprises from about 0.1% to about 10% by weight of the composition of a stabilizer, from about 5% to about 30% by weight of the composition of a lathering surfactant, and water.

DETAILED DESCRIPTION OF THE INVENTION

The present invention relates to liquid personal cleansing compositions which provide clinically efficacious moisturization to the skin. As used herein, "liquid personal cleansing compositions" refers to rinse-off personal cleansing products, including, but not limited to, shower washes, liquid handsoaps, and shampoos. The liquid personal cleansing compositions of the present invention are emulsions which contain a moisturizing phase comprising a lipophilic skin moisturizing agent and an aqueous cleansing phase comprising a surfactant, a stabilizer, and water. The lipophilic moisturizing agents which comprise the liquid personal cleansing compositions herein themselves comprise droplets which have a particle size distribution such that at least about 10% by weight of the droplets are greater than about 200 microns in diameter. For purposes of the present invention, the diameter of a particle means the longest length of the particle. It has been found that when at least about 10% by weight of the droplets comprising the lipophilic skin moisturizing agent are greater than about 200 microns in diameter, that the liquid personal cleansing composition which contains the lipophilic skin moisturizing agent will provide clinically efficacious moisturization to the skin.

Liquid personal cleansing compositions which contain lipophilic skin moisturizing agent wherein at least 10% by weight of the droplets have a diameter of greater than about 200 microns, including the materials contained therein and processes for preparing, are described in detail as follows:

I. Ingredients

A. Moisturizing Phase

The liquid personal cleansing emulsion compositions of the present invention comprise a moisturizing phase which comprises a lipophilic skin moisturizing agent. The liquid personal cleansing emulsion compositions of the present invention comprise from about 1% to about 30%, preferably from about 3% to about 25%, more preferably from about 5% to about 25% of a lipophilic skin moisturizing agent.

The lipid skin moisturizing agent provides a moisturizing benefit to the user of the personal cleansing product when the lipid moisturizing agent is deposited to the user's skin. It has been found that deposition of the lipophilic skin moisturizing agent is dramatically increased when at least about 10%, preferably at least about 20%, more preferably at least about 30%, even more preferably at least about 50% and most preferably at least about 80% by weight of the droplets comprising the lipophilic skin moisturizing agent have a droplet size of greater than about 200 microns, preferably greater than about 250 microns, more preferably greater than about 300 microns, even more preferably greater than about 500 microns, and most preferably greater than about 550 microns. In general, the larger the number of large particle-size lipophilic skin moisturizing agent and the larger the particle size of the lipophilic skin moisturizing agent, the greater the deposition of the moisturizing agent on the skin.

The lipophilic skin moisturizing agents suitable for use herein typically have a consistency (k) which ranges from about 5 poise to about 5,000 poise, preferably from about 10 poise to about 3,000 poise, more preferably from about 50 poise to about 2,000 poise, as measured by the Consistency Method hereinafter set forth in the Analytical Methods section. Suitable lipophilic skin moisturizing agents for use herein further have a shear index (n) ranging from about 0.1 to about 0.9, preferably from about 0.1 to about 0.5, more preferably from about 0.2 to about 0.5, as measured by the Shear Index Method hereinafter set forth in the Analytical Methods section.

While not being bound by any theory, it is believed that lipophilic skin moisturizing agents having rheology properties other than those defined herein are either too easily emulsified and hence will not deposit, or are too "stiff" to adhere or deposit on to skin and provide a moisturization benefit. In addition, the rheological properties of the lipophilic skin moisturizing agent are also important to user perception. Some lipophilic skin moisturizing agents, on deposition to the skin, are considered too sticky and are not preferred by the user.

In some cases, the lipophilic skin moisturizing agent can also desirably be defined in terms of its solubility parameter, as defined by *Vaughan in Cosmetics and Toiletries*, Vol. 103, p. 47–69, October 1988. A lipophilic skin moisturizing agent having a Vaughan solubility Parameter (VSP) of from 5 to 10, preferably from 5.5 to 9 is suitable for use in the liquid personal cleansing compositions herein.

A wide variety of lipid type materials and mixtures of materials are suitable for use as the lipophilic skin moisturizing agents in the personal cleansing compositions of the present invention. Preferably, the lipophilic skin conditioning agent is selected from the group consisting of hydrocarbon oils and waxes, silicones, fatty acid derivatives, cholesterol, cholesterol derivatives, di and tri-glycerides, vegetable oils, vegetable oil derivatives, liquid nondigestible oils such as those described in U.S. Pat. No. 3,600,186 to Mattson; Issued Aug. 17, 1971 and U.S. Pat. Nos. 4,005,195 and 4,005,196 to Jandacek et al; both issued Jan. 25, 1977, all of which are herein incorporated by reference, or blends of liquid digestible or nondigestible oils with solid polyol polyesters such as those described in U.S. Pat. No. 4,797, 300 to Jandacek; issued Jan. 10, 1989; U.S. Pat. Nos. 5,306,514, 5,306,516 and 5,306,515 to Letton; all issued Apr. 26, 1994, all of which are herein incorporated by reference, and acetoglyceride esters, alkyl esters, alkenyl esters, lanolin and its derivatives, milk-tri-glycerides, wax esters, beeswax derivatives, sterols, phospholipids and mixtures thereof. Fatty acids, fatty acid soaps and water soluble polyols are specifically excluded from our definition of a lipophilic skin moisturizing agent.

Hydrocarbon oils and waxes: Some examples are petrolatum, mineral oil micro-crystalline waxes, polyalkenes (e.g. hydrogenated and nonhydrogenated polybutene and polydecene), paraffins, cerasin, ozokerite, polyethylene and perhydrosqualene. Blends of petrolatum and hydrogenated and nonhydrogenated high molecular weight polybutenes wherein the ratio of petrolatum to polybutene ranges from about 90:10 to about 40:60 are also suitable for use as the lipid skin moisturizing agent in the compositions herein.

Silicone Oils: Some examples are dimethicone copolyol, dimethylpolysiloxane, diethylpolysiloxane, high molecular weight dimethicone, mixed C1–C30 alkyl polysiloxane, phenyl dimethicone, dimethiconol, and mixtures thereof. More preferred are non-volatile silicones selected from dimethicone, dimethiconol, mixed C1–C30 alkyl polysiloxane, and mixtures thereof. Nonlimiting examples of silicones useful herein are described in U.S. Pat. No. 5,011,681, to Ciotti et al., issued Apr. 30, 1991, which is incorporated by reference.

Di and tri-glycerides: Some examples are castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils and vegetable oil derivatives; coconut oil and derivatized coconut oil, cottonseed oil and derivatized cottonseed oil, jojoba oil, cocoa butter, and the like.

Acetoglyceride esters are used and an example is acetylated monoglycerides.

Lanolin and its derivatives are preferred and some examples are lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate.

It is most preferred when at least 75% of the lipophilic skin conditioning agent is comprised of lipids selected from the group consisting: petrolatum, blends of petrolatum and high molecular weight polybutene, mineral oil, liquid non-digestible oils (e.g. liquid cottonseed sucrose octaesters) or blends of liquid digestible or nondigestible oils with solid polyol polyesters (e.g. sucrose octaesters prepared from C22 fatty acids) wherein the ratio of liquid digestible or nondigestible oil to solid polyol polyester ranges from about 96:4 to about 80:20, hydrogenated or nonhydrogenated polybutene, micro-crystalline wax, polyalkene, paraffin, cerasin, ozokerite, polyethylene, perhydrosqualene; dimethicones, alkyl siloxane, polymethylsiloxane, methylphenylpolysiloxane and mixtures thereof. When as blend of petrolatum and other lipids is used, the ratio of petrolatum to the other selected lipids (hydrogenated or unhydrogenated polybutene or polydecene or mineral oil) is preferably from about 10:1 to about 1:2, more preferably from about 5:1 to about 1:1.

B. Aqueous Cleansing Phase

The liquid personal cleansing emulsion compositions of the present invention also comprise an aqueous cleansing phase which comprises a stabilizer, a lathering surfactant, and water. Each of these is described in detail as follows:

1. STABILIZER

The liquid personal cleansing compositions of the present invention also typically contain from about 0.1% to about 10%, preferably from about 0.25% to about 8%, more preferably from about 0.5% to about 5% of a stabilizer in the aqueous phase.

The stabilizer is used to form a crystalline stabilizing network in the emulsion that prevents the lipophilic skin moisturizer agent droplets from coalescing and phase splitting in the product. The network exhibits time dependent recovery of viscosity after shearing (e.g., thixotropy).

The stabilizers used herein are not surfactants. The stabilizers provide improved shelf and stress stability, but allow the oil-in-water emulsion to separate upon lathering, and thereby provide for increased lipid deposition onto the skin. This is particularly true when the oil-in-water cleansing emulsions of the present invention are used in conjunction with a polymeric diamond meshed sponge implement such as that described in Campagnoli; U.S. Pat. No. 5,144,744; Issued Sep. 8, 1992, herein incorporated by reference.

In one embodiment of the present invention, the stabilizer employed in the personal cleansing compositions herein comprises a crystalline, hydroxyl-containing stabilizer. This stabilizer can be a hydroxyl-containing fatty acid, fatty ester or fatty soap water-insoluble wax-like substance or the like.

The crystalline, hydroxy-containing stabilizer is selected from the group consisting of:

$$\begin{array}{c} CH_2-OR_1 \\ | \\ CH-OR_2 \\ | \\ CH_2-OR_3 \end{array} \quad (i)$$

wherein $R_1$ is $-\overset{O}{\underset{\|}{C}}-R_4(CHOH)_xR_5(CHOH)_yR_6$;

$R_2$ is $R_1$ or H
$R_3$ is $R_1$ or H
$R_4$ is $C_{0\text{-}20}$ Alkyl
$R_5$ is $C_{0\text{-}20}$ Alkyl,
$R_6$ is $C_{0\text{-}20}$ Alkyl
$R_4+R_5+R_6=C_{10\text{-}22}$
and wherein $1 \leq x+y \leq 4$;

$$R_7-\overset{O}{\underset{\|}{C}}-OM \quad (ii)$$

wherein
$R_7$ is $-R_4(CHOH)_xR_5(CHOH)_yR_6$
M is $Na^+$, $K^+$ or $Mg^{++}$, or H; and
iii) mixtures thereof;

Some preferred hydroxyl-containing stabilizers include 12-hydroxystearic acid, 9,10-dihydroxystearic acid, tri-9,10-dihydroxystearin and tri-12-hydroxystearin (hydrogenated castor oil is mostly tri-12-hydroxystearin). Tri-12-hydroxystearin is most preferred for use in the emulsion compositions herein.

When these crystalline, hydroxyl-containing stabilizers are utilized in the personal cleansing compositions herein, they are typically present at from about 0.5% to 10%, preferably from 0.75% to 8% more preferably from 1.25% to about 5% of the liquid personal cleansing compositions. The stabilizer is insoluble in water under ambient to near ambient conditions.

Alternatively, the stabilizer employed in the personal cleansing compositions herein can comprise a polymeric thickener. When polymeric thickeners as the stabilizer in the personal cleansing compositions herein, they are typically included in an amount ranging from about 0.01% to about 5%, preferably from about 0.3% to about 3%, by weight of the composition. The polymeric thickener is preferably an anionic, nonionic, cationic or hydrophobically modifier polymer selected from the group consisting of cationic polysaccharides of the cationic guar gum class with molecular weights of 1,000 to 3,000,000, anionic cationic and nonionic homopolymers derived from acrylic and/or methacrylic acid, anionic cationic and nonionic cellulose resins, cationic copolymers of dimethyldialkylammonium chloride and acrylic acid, cationic homopolymers of dimethylalkylammonium chloride, cationic polyalkylene and ethoxypolyalkylene imines, polyethylene glycol of molecular weight from 100,000 to 4,000,000, and mixtures thereof. Preferably, the polymer is selected from the group consisting of Sodium Polyacrylate, hydroxy ethyl Cellulose, Cetyl Hydroxy Ethyl Cellulose, and Polyquaternuium 10.

Another stabilizer which can be employed in the personal cleansing compositions herein are C10–C22 ethylene glycol fatty acid ester. C10–C22 ethylene glycol fatty acid esters can also desirably be employed in combination with the polymeric thickeners hereinbefore described. The ester is preferably a diester, more preferably a C14–C18 diester, most preferably ethylene glycol distearate. When C10–C22 ethylene glycol fatty acid esters are utilized as the stabilizer in the personal cleansing compositions herein, they are typically present at from about 3% to about 10%, preferably from about 5% to about 8%, more preferably from about 6% to about 8% of the personal cleansing compositions.

Another class of stabilizer which can be employed in the personal cleansing compositions of the present invention comprises dispersed amorphous silica selected from the group consisting of fumed silica and precipitated silica and mixtures thereof. As used herein the term "dispersed amorphous silica" refers to small, finely divided non-crystalline silica having a mean agglomerate particle size of less than about 100 microns.

Fumed silica, which is also known as arced silica, is produced by the vapor phase hydrolysis of silicon tetrachloride in a hydrogen oxygen flame. It is believed that the combustion process creates silicone dioxide molecules which condense to form particles. The particles collide, attach and sinter together. The result of this process is a three dimensional branched chain aggregate. Once the aggregate cools below the fusion point of silica, which is about 1710° C., further collisions result in mechanical entanglement of the chains to form agglomerates. precipitated silicas and silica gels are generally made in aqueous solution. See, Cabot Technical Data Pamphlet TD-100 entitled "CAB-O-SIL® Untreated Fumed Silica Properties and Functions", October 1993, and Cabot Technical Dat Pamphlet TD-104 entitled "CAB-O-SIL® Fumed Silica in Cosmetic and Personal Care Products", March 1992, both of which are herein incorporated by reference.

The fumed silica preferably has a mean agglomerate particle size ranging from about 0.1 microns to about 100 microns, preferably from about 1 micron to about 50 microns, and more preferably from about 10 microns to about 30 microns. The agglomerates are composed of aggregates which have a mean particle size ranging from about 0.01 microns to about 15 microns, preferably from about 0.05 microns to about 10 microns, more preferably from about 0.1 microns to about 5 microns and most preferably from about 0.2 microns to about 0.3 microns. The silica preferably has a surface area greater than 50 sq. m/gram, more preferably greater than about 130 sq. m./gram, most preferably greater than about 180 sq. m./gram.

When amorphous silicas are used as the stabilizer herein, they are typically included in the emulsion compositions at levels ranging from about 0.1% to about 10%, preferably from about 0.25% to about 8%, more preferably from about 0.5% to about 5%.

A fourth class of stabilizer which can be employed in the personal cleansing compositions of the present invention comprises dispersed smectite clay selected from the group consisting of bentonite and hectorite and mixtures thereof. Bentonite is a colloidal aluminum clay sulfate. See Merck Index, Eleventh Edition, 1989, entry 1062, p. 164, which is incorporated by reference. Hectorite is a clay containing sodium, magnesium, lithium, silicon, oxygen, hydrogen and flourine. See Merck Index, eleventh Edition, 1989, entry 4538, p. 729, which is herein incorporated by reference.

When smectite clay is employed as the stabilizer in the personal cleansing compositions of the present invention, it is typically included in amounts ranging from about 0.1% to about 10%, preferably from about 0.25% to about 8%, more preferably from about 0.5% to about 5%.

2. THE LATHERING SURFACTANT

The personal cleansing emulsion compositions of the present invention also comprises a lathering surfactant selected from the group consisting of anionic surfactants; nonionic surfactants, cationic surfactants, amphoteric surfactants, and mixtures thereof.

The lathering surfactant is defined herein as a surfactant or surfactant mixture thereof that when combined have an equilibrium surface tension of between 15 and 50 dynes/cm, more preferably between 25 and 40 dynes/cm as measured at the CMC (critical micelle concentration) at 25° C. Some surfactant mixes can have a surface tension lower than those of its individual components.

The personal cleansing compositions herein comprise from about 5% to about 30%, preferably from about 5% to about 25%, and most preferably from about 10% to about 25% of a lathering surfactant.

Anionic surfactants useful herein include: acyl isethionates, acyl sarcosinates, alkylglycerylether sulfonates, alkyl sulfates, alkyl sulfates, acyl lactylate, methylacyl taurates, paraffin sulfonates, linear alkyl benzene sulfonates, N-acyl glutamates, alkyl sulfosuccinates, alpha sulfo fatty acid esters, alkyl ether carboxylates, alkyl phosphate esters, ethoxylated alkyl phosphate esters,, alpha olefin sulphates, the alkyl ether sulfates (with 1 to 12 ethoxy groups) and mixtures thereof, wherein said surfactants contain C8 to C22 alkyl chains and wherein the counterion is selected from the group consisting of: Na, K, $NH_4$, $N(CH_2CH_2OH)_3$. The anionic surfactant is more preferred when selected from the group consisting of acyl isethionate, acyl sarcosinates, acyl lactylates, alkyl sulfosuccinates, alkylglycerylether sulfonates, methylacyl taurates, alkyl ether sulfates, alkyl sulfates, alkyl phosphate esters and mixtures thereof, wherein said surfactants contain has C8 to C14 alkyl chains and is present at a level of from about 8% to about 20%.

Amphoteric synthetic surfactants cannot serve as the sole surfactant in this product, but are preferred as a co-surfactant at a lower level of from about 1 part to about 10 parts, by weight and the more preferred types are selected from alkyl-ampho mono- and di-acetates, alkyl amidopropyl betaines, alkyl dimethyl amine oxides, alkyl sultaines, alkyl amidopropyl betaines, alkyl amidopropyl hydroxysultaines, and mixtures thereof, wherein said surfactants contain C8 to C22 alkyl chains.

Nonionic synthetic surfactant cannot serve as the sole surfactant in this product, but can be used as a co-surfactant at a lower level of from about 1% to about 15% by weight. The more preferred types selected from the group consisting: alkyl glucose amides, alkyl glucose esters, polyoxyethylene amides, fatty alkane amides, alkyl amine oxides, alkyl polyglucosides, polyoxy ethylene alkyl phenols, polyoxyethylene esters of fatty acids, EO/PO block co-polymers such as polyoxarmines and poloxamers, sorbitan esters and alcohol esters, and mixtures thereof.

Cationic synthetic surfactant cannot serve as the sole surfactant in this product, but are preferred as a co-surfactant at a lower level of from about 0.5% to about 6%, by weight. The more preferred types of cationic surfactants are selected from the group consisting: alkyl trimonium chloride and methosulfate, and dialkyldimonium chloride and methyl sulphate, and alkyl alkonium chloride and methyl sulphate and mixtures thereof. These surfactants contain C12 to C24 carbon atoms per alkyl chain. The most preferred cationic is selected from the group consisting of stearalkonium chloride, stearyltrimonium chloride, Di-stearyl-dimonium chloride, and mixtures thereof. Cationic surfactants may also act as a lipid deposition aid.

The liquid emulsions compositions herein can also optionally contain C8–C14 fatty acid soap; where the soap has a counterion selected from the group consisting of K and $N(CH2CH2OH)_3$, and mixtures thereof, in addition to the lathering synthetic surfactant. In one preferred embodiment of the present invention, the liquid personal cleansing compositions comprise less than about 5%, preferably less than about 4%, more preferably less than about 3%, and most preferably less than about 2% by weight of fatty acid soap.

3. WATER

The moisturizing personal cleansing emulsion compositions of the present invention comprise water as an essential component. The water is typically present at a level of from about 30% to about 80%, preferably from about 40% to about 75%, and most preferably from about 40% to about 65% of the personal cleansing compositions of the present invention.

4. OPTIONAL INGREDIENTS

The personal cleansing compositions of the present invention can also contain a number of optional ingredients in the aqueous phase.

For example, the liquid personal cleansing compositions of the present invention can optionally include water-dispersible, gel-forming polymers. This polymer is preferably a anionic, nonionic, cationic or hydrophobically modified polymer, selected from the group consisting of cationic polysaccharides of the cationic guar gum class with molecular weights of 1,000 to 3,000,000, anionic, cationic and nonionic homopolymers derived from acrylic and/or methacrylic acid, anionic, cationic and nonionic cellulose resins; cationic copolymers of dimethyldialkylammonium chloride and acrylic acid; cationic homopolymers of dimethyldialkylammonium chloride; cationic polyalkylene and ethoxypolyalkylene imines polyethylene glycol of molecular weight from 100,00 to 4,000,000; and mixtures thereof. Preferably, the polymer is selected form the group consisting of Sodium Polyacrylate, Hydroxy Ethyl Cellulose, Cetyl Hydroxy Ethyl Cellulose, and Polyquaternium 10.

The polymer is preferably included in the compositions of the present invention at a level of from about 0.1 parts to 1 part, more preferably 0.1 parts to 0.5 parts. The polymers can improve the sensory feel of the lipid on skin in addition to providing product stabilization. The improved sensory feel results from reduced tackiness and greasiness and improved smoothness. It is an especially preferred embodiment to use mixture of polymers, some of which are preferred for product stabilization, some are preferred for improved sensory feel. Preferred polymers to improve sensory feel are selected from the group consisting: of polyethylene glycol, hydroxypropyl guar, guar hydroxypropyltrimonium chloride, polyquaternary 3, 5, 6, 7, 10, 11 and 24 and mixtures thereof.

Another highly preferred optional component of the present compositions are one or more humectants and solutes. A variety of humectants and solutes can be employed and can be present at a level of from about 0.5% to about 25%, more preferably from about 3.0% to about 20%. The humectants and solutes are non-volatile, organic materials having a solubility of a least 5 parts in 10 parts water. A preferred water soluble, organic material is selected from the group consisting of a polyol of the structure:

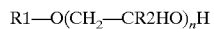

where R1=H, C1–C4 alkyl; R2=H, $CH_3$ and n=1–200; C2–C10 alkane diols; guanidine; glycolic acid and glycolate salts (e.g. ammonium and quaternary alkyl ammonium); lactic acid and lactate salts (e.g. ammonium and quaternary alkyl ammonium); polyhydroxy alcohols such as sorbitol, glycerol, hexanetriol, propylene glycol, hexylene glycol and the like; polyethylene glycol; sugars and starches; sugar and starch derivatives (e.g. alkoxylated glucose); panthenol (including D-, L-, and the D,L-forms); pyrrolidone carboxylic acid; hyaluronic acid; lactamide monoethanolamine; acetamide monoethanolamine; urea; and ethanol amines of the general structure $(HOCH_2CH_2)_xNH_y$ where x=1–3; y=0–2, and x+y=3, and mixtures thereof. The most preferred polyols are selected from the group consisting of glycerine, polyoxypropylene(1) glycerol and polyoxypropylene(3) glycerol, sorbitol, butylene glycol, propylene glycol, sucrose, urea and triethanol amine.

Preferred water soluble organic material are selected from the group consisting of glycerine, polyoxypropylene (1) glycerol and polyoxypropylene (3) glycerol, sorbitol, butylene glycol, propylene glycol, sucrose, and urea and triethanolamine.

The use of oil thickening polymers, such as those listed in EP 0 547 897 A2 to Hewitt, published 23 Jun. 1993, incorporated herein by reference, can also be included in the water phase of the emulsions of the present invention.

A variety of additional ingredients can be incorporated into the compositions of the present invention. These materials including, but not limited to, liquid appearance aids, salts and their hydrates and other "filler materials" are listed in U.S. Pat. No. 5,340,492, to Kacher et al., issued Aug. 23, 1994, and U.S. Pat. No. 4,919,934, to Deckner et al., issued Apr. 24, 1990; which is incorporated herein by reference.

Other non limiting examples of these additional ingredients include vitamins and derivatives thereof (e.g., ascorbic acid, vitamin E, tocopheryl acetate, and the like); sunscreens; thickening agents (e.g., polyol alkoxy ester, available as Crothix from Croda at levels up to 2% and xanthan gum at levels up to about 2%); preservatives for maintaining the anti microbial integrity of the compositions; antiacne medicaments (resorcinol, salicylic acid, and the like); antioxidants; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), additives to impart a draggy rinse feel (e.g., fumed silica), additives to enhance deposition (e.g., maleated soybean oil at levels up to 3%), lakes, colorings, and the like (e.g., clove oil, menthol, camphor, eucalyptus oil, and eugenol).

II. Process for Preparing the Moisturizing Liquid Personal Cleansing Emulsion Compositions Herein In one preferred embodiment of the present invention, liquid personal cleansing emulsions which contain lipophilic skin moisturizing agents wherein the droplets have the requisite particle size are prepared by encapsulating the lipophilic skin moisturizing agents within a complex coascervate to protect the integrity of the large droplets during the processing and packaging of the cleansing compositions. However, in order the obtain the moisturizing benefit, the lipophilic skin moisturizing agent must be able to deposit on the skin. Therefore, the complex coascervate which encapsulates the lipophilic skin moisturizing agent during the processing of the liquid personal cleansing composition must be of a nature such that it will still allow the lipophilic skin moisturizing agent contained within to deposit on the skin.

The key factors affecting the ability of the complex coascervate to protect the integrity of the particles during processing and still allow the moisturizing agent to deposit on the skin are the relative hardness/softness of the complex coascervate and the thickness of the complex coascervate. In particular, the complex coascervate must be hard enough and thick enough to protect the integrity of the lipophilic skin moisturizing agent particles during processing of the liquid personal cleansing compositions, but soft enough and thin enough to allow the lipophilic skin moisturizing agent encapsulated within to deposit on the skin. It has been found that a suitable hardness for the complex coascervate ranges from about 50 to about 1400 grams force, preferably from about 400 to about 1200 grams force, more preferably from about 600 to about 1000 grams force, as measured by the Strength of Coascervate Method hereinafter described in the Analytical Methods section. It has further been found that the complex coascervate is of suitable thickness when at least about 10%, preferably at least about 30%, more preferably at least about 50%, and most preferably at least about 70% of the encapsulated lipophilic skin moisturizing agent particles are nonspherical in the final product. For purposes of the present invention, nonspherical particles are those particles having an aspect ratio (length divided by width) of greater than 1.1. It is believed that the nonspherical shape of the particles is directly related to the thickness of the complex coascervate and that the thickness of the complex coascervate is directly proportional to the deposition at a given particle size distribution.

The coascervate employed in this embodiment of the invention is a complex of a polycation having a minimum filtrate weight of about 10 grams and a polyanion. The complex coascervate typically comprises from about 0.1% to about 15%, preferably from about 0.5% to about 10%, more preferably from about 1% to about 5% polycation and from about 0.01% to about 10%, preferably from about 0.05% to about 5%, more preferably from about 0.1% to about 1% polyanion. The ratio of polycation to polyanion in the temporary complex coascervate ranges from about 30:1 to about 1:5, preferably from about 20:1 to about 1:2, more preferably from about 15:1 to about 1:1. Typically from about 50% to about 95% of each capsule consists of the lipophilic skin moisturizing agent. The ratio of the lipophilic skin moisturizing agent to the coascervate complex typically ranges from about 5:1 to about 1:5, preferably from about 3:1 to about 1:3, more preferably from about 2:1 to about 1:2.

When this method for preparing the liquid personal cleansing emulsion compositions of the present invention is employed, the compositions comprise from about 1% to about 35%, preferably from about 5% to about 30%, more preferably from about 10% to about 25% of the encapsulated lipophilic skin moisturizing agent. The amount of encapsulated lipophilic skin moisturizing agent that is included in the personal cleansing compositions is an amount such that the composition contains from about 1% to about 30%, preferably from about 3% to about 25%, more preferably from about 5% to about 25% of lipophilic skin moisturizing agent. Typically, the personal cleansing composition will contain from about 0.1% to about 5%, preferably from about 0.3% to about 3%, more preferably from about 0.5% to about 1.5% of the polycation and from about 0.01% to about 1%, preferably from about 0.02% to about 0.5%, more preferably from about 0.03% to about 0.2% of the polyanion.

Polycations which are suitable for use in this embodiment for preparing the compositions of the present invention have a minimum filtrate weight of about 10 grams, preferably about 15 grams, more preferably about 20 grams, as measured by the Filtrate Weight Method set forth hereinafter in the Analytical Methods section. Polycations having a filtrate weight of less than about 10 grams will not form a thick enough coascervate, when combined with the polyanion, to protect the integrity of the lipophilic skin moisturizing agent particles during processing of the liquid personal cleansing composition.

Proteins having a average molecular weight ranging from about 50 to about 1,000,000 are preferred polycations for use in this embodiment for preparing the compositions of the present invention. Preferred proteins for use herein include, for example, gelatin, ovalbumin, serum albumin, casein, chitin, and mixtures thereof.

Gelatin is an especially preferred protein for use as a polycation in this embodiment for preparing the compositions of the present invention. Gelatins can be characterized according to bloom strength. Bloom strength is the force (measured in grammes) required to depress the surface of a 6 3/3% w/w gel, matured at 10° C. for 16–18 hours, a distance of 4 mm using a flat-bottomed plunger 12.7 mm in diameter. The instrument used is the Bloom Gelometer. A semi-automated version, the Bloom Electronic Jelly Tester, can also be used Gelatins having a bloom strength ranging from about 60 to about 300, preferably from about 100 to about 300, more preferably from about 150 to about 300 and most preferably from about 200 to about 300 are suitable for use herein.

Other polycations having the requisite filtrate weight, such as polyvinylamine and cellulose derivatives, may also suitably be employed for use herein.

The polyanions suitable for use herein include, for example, polyphosphate, gum arabic, sodium alginate, carrageenan, cellulose acetate, phthalate, pectin, carboxymethylcellulose, ethylene maleic anhydride, and mixtures thereof.

Polyphosphate is an especially preferred polyanion for use herein.

The encapsulated lipophilic skin moisturizing agent can be prepared by preparing a hot aqueous solution of a polycation and a polyanion at a temperature greater than the melting point of the lipophilic skin moisturizing agent, and mixing in the lipophilic skin condition agent under low shear conditions, without utilizing a cross linking agent. When the polycation is gelatin, the pH is adjusted to within the range of from about 3.5 to about 5.0. The polycation and the polyanion complex to form a coascervate, and, upon cooling, the coascervate separates as a wall which encapsulates the lipophilic skin moisturizing agent.

It is important that the mixture of polycation, polyanion and lipophilic skin moisturizing agent be essentially free of cross-linking agent in order to ensure that the complex coascervate has the requisite hardness characteristics. When substantial amounts of a cross linking agent are employed herein, the complex coascervate will be too hard to allow the lipophilic skin moisturizing agent contained therein to deposit on the skin. As used herein "essentially free of cross-linking agent" means that the mixture contains less than about 0.25% of cross-linking agent. Cross-linking agents are elements, groups or compounds which bridge together two chains of polymer molecules by joining certain carbon atoms of the chains by primary chemical bonds. Cross-linking agents include for example, gluteraldehyde, urea, formaldehyde, phenol, tannic acid, and mixtures thereof.

When the lipophilic skin moisturizing agents are encapsulated, the particle size of the lipophilic skin moisturizing agent is a function of the RPM of the mixer, the composition of the aqueous solution and the rheology of the aqueous solution. In general, the lower the RPM of the mixer, the larger the particle size of the encapsulated lipophilic skin moisturizing agent. Also, to achieve a larger particle size for the encapsulated lipophilic skin moisturizing agent, the aqueous solution is preferably void of emulsifiers, such as surfactants, and should be essentially of a newtonian and nonviscous rheology.

When the encapsulated lipophilic skin moisturizing agent particles are mixed into the personal cleansing matrix, the amount of stress that is applied to the encapsulated particles is such that at least about 10% of the encapsulated particles in the final product are nonspherical.

Another way to prepare liquid personal cleansing emulsion compositions which contain lipophilic skin moisturizing agents having the requisite particle size is to incorporate the lipophilic moisturizing agent into the liquid personal cleansing matrix under very low shear conditions. Conventional incorporation techniques (e.g., batch agitated tank mixing and line static mixing) are capable of applying low shear. In order to achieve low shear when using a batch agitated tank, low rpm is used. In order to achieve low shear when using a static mixer, the number of elements is minimized, the diameter is maximized and the flow rate is minimized. Kock or Kenics static mixers can be employed in this embodiment for preparing the moisturizing liquid personal cleansing compositions of the present invention.

III. Characteristics of the Liquid Personal cleansing Compositions Herein

In order to achieve the deposition benefits hereinbefore described and to be consumer-acceptable, it is important that the liquid personal cleansing compositions of the present invention have particular rheological characteristics. In particular, the liquid personal cleansing compositions of the present invention have a viscosity ranging from about 2,000 centipoise to about 100,000 centipoise, preferably from about 5,000 centipoise to about 70,000 poise, more preferably from about 10,000 centipoise to about 40,000 centipoise and a yield point ranging from about 5 to about 90 dynes/sq. cm., preferably from about 7 to about 50 dynes/sq. cm., more preferably from about 9 to about 40 dynes/sq. cm., and most preferably from about 11 to about 30 dynes/sq. cm., as measured by the Yield Point Method hereinafter set forth in the Analytical Methods Section.

The liquid personal cleansing compositions of the present invention provide clinically efficacious moisturization benefits to the skin. It is believed that this is due to the dramatically increased deposition of lipophilic skin moisturizing agent comprised of relatively large droplets compared to lipophilic skin moisturizing agents comprised of smaller droplets. The liquid personal cleansing compositions of the present invention have a Deposition Value of at least about 10 micrograms/square centimeter, preferably at least about 15 micrograms/square centimeter, more preferably at least about 20 micrograms/square centimeter, and most preferably at least about 30 micrograms/square centimeter of lipophilic skin moisturizing agent on the skin as measured by the Deposition Method set forth hereinafter in the Analytical Methods section.

Analytical Methods

A number of parameters used to characterize elements of the present invention are quantified by particular experimental analytical procedures. Each of these procedures are described in detail as follows:

1. Consistency (k) and Shear Index (n) of the Lipophilic Skin Moisturizing Agent The Carrimed CSL 100 Controlled Stress Rheometer is used to determine Shear Index, n, and Consistency, k, of the lipophilic skin moisturizing agent used herein. The determination is performed at 35° C. with the 4 cm 2° cone measuring system typically set with a 51 micron gap and is performed via the programmed application of a shear stress (typically from about 0.06 dynes/sq. cm to about 5,000 dynes/sq. cm) over time. If this stress results in a deformation of the sample, i.e. strain of the measuring geometry of at least 10–4 rad/sec, then this rate of strain is reported as a shear rate. These data are used to create a viscosity $\mu$ Vs. shear rate $\gamma'$ flow curve for the material. This flow curve can then be modeled in order to provide a mathematical expression that describes the material's behavior within specific limits of shear stress and shear rate. These results were fitted with the following well accepted power law model (see for instance: *Chemical Engineering,* by Coulson and Richardson, Pergamon, 1982 or *Transport Phenomena* by Bird, Stewart and Lightfoot, Wiley, 1960):

$$\text{Viscosity, } \mu = k(\gamma')^{n-1}$$

2. Viscosity of the Liquid Personal Cleansing Composition

The Wells-Brookfield Cone/Plate Model DV-II+ Viscometer is used to determine the viscosity of the liquid personal cleansing compositions herein. The determination is performed at 25° C. with the 2.4 cm° cone (Spindle CP-41) measuring system with a gap of 0.013 mm between the two small pins on the respective cone and plate. The measurement is performed by injecting 0.5 ml of the sample to be analyzed between the cone and plate and toating the cone at a set speed of 1 rpm. the resistance to the rotation of the one produces a torque that is proportional to the shear stress of the liquid sample. The amount of torque is read and computed by the viscometer into absolute centipoise units (mPa*s) based on geometric constants of the cone, the rate of rotation, and the stress related torque.

3. Deposition of the Lipophilic Skin Moisturizing Agent

A. Preparation

The arms are washed with a nonsoap-containing, nonlipid-containing product to reduce background interference as much as possible, then blotted dry. The subject then wets the entire surface of the inner forearm with 95–100 F. tap water for five seconds. The subject then saturates a puff, such as that described in Campagnoli; U.S. Pat. No. 5,144, 744; Issued Sep. 8, 1992, and allows the puff to drain for 10 seconds. One milliliter of the liquid personal cleansing composition which contains the lipophilic skin moisturizing agent is applied to the forearm of the subject and then the product is rubbed with the puff for 10 seconds to generate lather. The lather is allowed to remain on the forearm for fifteen seconds, followed by a thorough rinse for fifteen seconds with the water flowing from inner elbow to wrist. The subject arm is then pat dried with a paper towel. The subject then allows the arm to "air" dry for 30 seconds.

B. Deposition Protocol—Sebumeter

Deposition of the lipophilic skin moisturizing agent on the skin is measured using a a Sebumeter SM810 which is commercially available from Courage and Khazaka GmbH. The Sebumeter measures the amount of lipophilic skin moisturizingagent that has been deposited on the skin via photometry of a special plastic strip, which becomes transparent when it absorbs the lipophilic skin moisturizing agent. The plastic strip is extended over a mirror which is connected to a spring. The measuring head of the device (comprised of spring, mirror and plastic strip) is pressed against the skin for 30 seconds. The Deposition Value ($\mu$g/sq. cm) is indicative of the amount of lipophilic skin moisturizing agent on the skin; the Deposition Value increases with increased amount of lipophilic skin moisturizing agent. The method is insensitive to humidity. Sebumeter readings (3) are taken along the length of the forearm and the Deposition Value ($\mu$g/sq. cm) is defined as the mean of the 3 readings, divided by a conversion factor to translate the sebumeter readings to actual deposition levels in $\mu$g/sq. cm.

The Sebumeter has the following limitations:

1. The Sebumeter tape also detects natural skin lipids. A criterion of this test is that subjects baseline value measured on the Sebumeter, prior to washing, be less than or equal to 3 $\mu$g/sq. cm of forearm skin.

2. The Sebumeter like other surface extraction measurements may not measure all the deposited lipophilc skin moisturizing agent; if the skin topography is undulating it is possible that deposited lipophilic skin moisturizing agent may not be extracted by the Sebumeter tape.

3. The Sebumeter tape becomes saturated at a Deposition Value of above about 300 $\mu$g/sq. cm; so this method can only measure deposition values up to about 300 $\mu$g/sq. cm.

4. Different lipophilic skin moisturizing agents will have different conversion factors. For testing non-petrolatum lipids, a new calibration curve is required.

C. Calibration

To translate the Sebumeter data obtained as hereinbefore described into deposition data, it is necessary to generate a conversion factor. To generate the conversion factor, an extraction is done for each lipid system and the extracted sample is analyzed by gas chromatography. The extraction is done at the same time as the Sebumeter reading and is taken from the same forearm. The extraction procedure is as follows:

1) An open-ended glass cylinder (2 inches in diameter) is placed onto the subject's inner forearm and securely strapped in place.

2) Five ml of extraction solvent is added to the cylinder.

3) The liquid is stirred on the subject's arm for 30 seconds using a blunt-ended glass stirring rod. The full surface area of the enclosed forearm is treated with solvent.

4) The liquid is transferred to a 6 dram vial using a disposable transfer pipet.

5) Steps 2–5 are repeated two times (total of three samples, 15 ml of solvent collected)

The extracted sample is then analyzed by gas chromatography as follows:

| APPARATUS | |
|---|---|
| Gas Chromatograph | HP 5890 or equivalent equipped with capillary inlet system and flame ionization detector. |
| Integration System | PEN Turbochrom v4.0 data system, or HP 3396 Series II integrator, or equivalent with peak-grouping capability. |
| Column | DB-5ht, 30M × 0.32 mm I.D., 0.10 $\mu$m film thickness, J&W Scientific cat. no. 123-5731. |
| Analytical Balance | Capable of weighting to 0.0001 g. |
| Pipet | 1 mL, Class A. |
| Volumetric Flask | 1000 mL, 100 mL, glass stoppered. |
| Glass Syringe | 100 $\mu$L capacity |
| Autosampler Vials | With crimp-top caps |
| Dry Bath | Regulated at 80–85° C. |
| Pipettor | Ependorf Repeator with 12.5 mL reservoir |
| Stir Plate and Stir Bars | Teflin-coated stir bars |

-continued

| REAGENTS | |
|---|---|
| Heptane | ACS grade. |
| Squalane | Aldrich cat. no. 23,431-1 or equivalent. |
| Lipid Standard | |
| GC CONDITIONS | |
| Carrier Gas | Helium UHP grade or regular grade helium purified through a dry tube and an oxygen scrubber. Flow pressure regulated at 25 psi with 25 ml/min split. |
| Injection Mode | Splitless |
| Injection Volume | 2 µl |
| Injector Temperature | 310° C. |
| Oven Temperature Program | 100° C. for 0 minutes @ 10° C./min. to 350° C.; hold for 6 min. |
| Detector Temperature | 350° C. |
| Hydrogen and Air Flows | Optimized for gas chromatograph used. |
| Bunching Factor | 2 |
| SOLUTIONS | |
| Internal Standard Solution | Into a clean, dry 100 mL volumetric flask, analytically weight 0.1 g of squalane, recording weight to nearest 0.0002 g. Dilute to volume with heptane, stopper and stir to dissolve. (A 1:1000 dilution of this solution can be used as the extraction solvent when generating samples.) |
| Lipid Stock Solution | Into a clean, dry 100 ml volumetric flask, analytically weight 0.5 gram of lipid standard, recording weight to nearest 0.0002 g. Dilute to volume with heptane, stopper and stir to mix. |
| Lipid Working Standards | Label three autosampler vials as follows: "100 µg," "300 µg" and "500 µg." Using the glass syringe, transfer 15 µL of internal standard solution into each vial. Rinse syringe well with heptane, then use it to transfer the following amounts of lipid stock solution to the vials:<br><br>Std.    Vol. Stock Soln. (µL)<br>100 µg    20<br>300 µg    60<br>500 µg    100<br>Dilute to approx. 0.5 mL with heptane, then cap and shake to mix. |
| OPERATION | |
| 1. Calibration | Run each standard under the above conditions. Select the 10–14 largest peaks from the calibration run and create a peak group within the calibration of the method. Assign the amount of lipid in the standard to the group for each calibration level. Plot the area ratio on the y-axis. Do not force the line through the origin or include the origin. The r2 value should be at least 0.9990. Check calibration every ten or twelve samples and at the end of the sample run. |
| 2. Sample Analysis | Evaporate samples to dryness under a stream of dry nitrogen. Reconstitute in 0.5 mL heptane. Cap tightly and place on dry bath for 5 minutes; shake to dissolve completely. Transfer to autosampler vials and analyze on calibrated instrument with the proper ISTD amount entered. Important: Because the baseline is cluttered, manually check each result file for correct peak identification. |

The GC data is then plotted on a curve versus the Sebumeter data. The slope of the curve is the conversion factor. The conversion factor for petrolatum is 0.56.

4. Filtrate weight of Polycation

The filtrate weight of a polycation is measured via a filtration apparatus which utilizes mechanical suction to effectively filter out the polycation coacervate.

The complex coascervate is formed by mixing together dissolved polycation and dissolved sodium hexametaphosphate (Glass H from FMC Corporation—average $P_2O_5$ chain length of 21. The total amount of combined polycation and hexametaphosphate to be mixed together is 12 grams. The ratio of polycation to hexametaphosphate to be employed is ratio at which a precipitate is formed. When gelatin is the polycation, the ratio of gelatin to hexametaphosphate to be employed is 11:1 (e.g., 11 grams of gelatin and 1 gram of hexametaphosphate).

Once the proper amounts of polycation and hexametaphosphate to be mixed together has been calculated as described above, both the polycation and the hexametaphosphate are dissolved in de-ionized water with heating and stirring. The total amount of water to be used for dissolving the polycation ad the hexametaphosphate is 286 grams. The hexametaphosphate is dissolved in 19× by weight water. The polycation is dissolved in the remainder of the water.

After the polycation and the hexametaphosphate have been separately dissolved, the two solutions are mixed together. When gelatin is used as the polycation, the pH is then adjusted to 3.7 with glacial acetic acid added drop-wise while stirring. The resultant mixture is then cooled to room temperature to induce a phase separated coascervate polycation/hexametaphosphate/water complex which can be filtered and weighed.. The coascervate complex is filtered from the solution via a setup consisting of a 1000 ml Erlenmeyer Flask, 100 mm porcelain Buchner funnel, and 90 mm medium porosity/medium flow rate Whatman grade No. 40 filter paper. The mechanical suction is provided via a ⅙ horsepower Gast vacuum pump. The filtered coascervate complex is weighed and the weight is reported in grams as the filtrate weight of polycation.

5. Particle Size Distribution for Lipophilic Skin Moisturizing Agent Particles

The particle size distribution of the lipophilic skin moisturizing agent is estimated via a scanning laser microscope which is commercially produced by Lasentec (Lasentec M100F). The lasentec M100F measures suspended particles by scanning a focused laser beam at a constant velocity across particles suspended in the liquid and moving past the window of a probe. When the focal point intercepts a particle, some light is scattered back to the probe and converted to an electronic pulse, which is converted to size by the relationship: d=v*t. The duration of the pulse represents the time (t) the particle is illuminated in the focal point. Because the velocity (v) of the focal spot is known, (d) is therefore the scanned distance across the particle. This distance represents the length of a chord of the particle. The chord length distribution is an accurate direct measure of the particle structure dimensions and particle structure shate as determined on a 3-dimensional basis. The M100 classifies particles into 38 channels, ranging from 1.9 to 1000 microns. The particle size distribution is generated using a length cube weight average chord calculation which gives an estimate of the amount of substance per particle size (versus the number of particles per particle size):

$$\text{Length Cube Weight Average Chord} = \frac{\sum_{i=1}^{k} n_i m_i^4}{\sum_{i=1}^{k} n_i m_i^3}$$

$n_i$ = Counts in an individual measurement channel $M_i$ = Midpoint of an individual channel k = Upper channel # (2 ≤ k ≤ 38)

The lasentec measures the particle size distribution of everything within the formula including precipitates and air pockets. Therefore, light microscopy is used as a supplemental lipophilic moisturizing agent particle size measurement technique to confirm the data generated by the Lasentec M100F. In this technique, the product is viewed under very low magnification (<10×) between a plate and coverslip and lipophilic moisturizing agent particles sizes are estimated via a micrometer.

6. Yield Point of Liquid Personal Cleansing Compositions

The Carrimed CSL 100 Controlled Stress Rheometer is used to determine the yield point of the liquid personal cleansing compositions. As used herein, the yield point is the amount of stress required to produce a strain of 1% on the liquid personal cleansing composition. The determination is performed at 77° F. with the 4 cm 2° cone measuring system set with a 51 micron gap. the determination is performed via the programmed application of a shear stress (typically from about 0.06 dynes/sq. centimeter to about 500 dynes/square centimeter) over time. If this amount of stress results in a deformation of the sample, a shear stress vs. strain curve can be created. From this curve, the yield point of the liquid personal cleansing composition can be calculated.

7. Strength of the Complex Coacervate

A. Preparation

The complex coacervate is formed by combining the formula amounts of the desired polycation and polyanion in aqueous solution. When the polycation is gelatin, the pH is adjusted to within the range of 3.5 to 4.5 by adding glacial acetic acid drop-wise. The resultant mixture is cooled to induce a phase separated coacervate. The supernatant is decanted, and enough of the complex coacervate is transferred to a petri culture dish (100×15 mm) to completely fill the dish and leave a flat surface flush with the top of the dish. The sample is them allowed to equilibrate at room temperature for 24 hours.

B. Strength Protocol

The Stable MicroSystems Universal TA.XT2 Texture Analyser and the XT.RA Dimension data acquisition system is used to measure the strength of the complex coacervate. The Texture Analyser uses a cylindrical probe (14×11.5 mm) to measure force in compression of the complex coacervate. The probe is set within 2 mm of the top of the complex coacervate sample. The probe pushes down to a trigger force of 5 grams at the speed of 1 mm/sec. this is followed by a 4 mm compression distance at the entrance and exit speeds of 1 mm/sec. The data acquisition system records the required force in compression versus time. The maximum force in compression is recorded as the strength of the complex coacervate.

8. Method for Determining % Nonspherical Particles

A stereo binocular scope (Zeiss SV8) is utilized to determine the % nonspherical particles in the final product. Typically, pictures are taken of the final product at a magnification ranging from 9.5× to 24×. Using the pictures, the number of nonspherical particles (as hereinbefore defined) in the picture is counted. The % nonspherical particle is determined by dividing the number of nonspherical particles by the total number of particles.

EXAMPLES

The following shower gel compositions are non-limiting examples of the liquid personal cleansing compositions of the present invention.

| Ingredients | #1 | #2 | #3 | #4 |
|---|---|---|---|---|
| Encapsulated Particles Pre-mix Composition: | | | | |
| Gelatin type A; 150 Bloom Strength | 2.21 | 0.0 | 0.0 | 0.0 |
| Gelatin type A, 100 Bloom Strength | 0.0 | 2.21 | 0.0 | 0.0 |
| Gelatin type A, 275 Bloom Strength | 0.0 | 0.0 | 2.21 | 1.98 |
| Hexameta Polyphosphate | 0.20 | 0.20 | 0.20 | 0.18 |
| Petrolatum | 40.16 | 40.16 | 40.16 | 35.42 |
| Glacial Acetic Acid (dropwise till pH <4.4) | ~0.08 | ~0.08 | ~0.08 | ~0.08 |
| De-ionized Water (Most in Excess) | QS | QS | QS | QS |
| Final Formula with Incorporated Filtered Particles: | | | | |
| Ammonium Lauryl Sulfate | 2.14 | 2.14 | 2.89 | 4.3 |
| Ammonium Laureth-3 Sulfate | 6.42 | 6.42 | 8.66 | 6.5 |
| Sodium Lauroamphoacetate | 3.67 | 3.67 | 4.95 | 4.7 |
| Fatty Acid Soap | 0.0 | 0.0 | 0.0 | 0.0 |
| Lauric Acid | 1.4 | 1.4 | 1.4 | 1.4 |
| Trihydroxystearin | 0.38 | 0.38 | 0.75 | 0.4 |
| Optional Ingredients | 4.53 | 4.53 | 4.39 | 5.0 |
| Encapsulated Petrolatum Particles (from Pre-mix) | 23.57 | 23.57 | 16.4 | 11.0 |
| Water | QS | QS | QS | QS |
| Lather (Ultimate Volume) | 450 | 450 | 390 | 550 |
| Deposition ($\mu$g/cm$^2$) | 69 | 43 | 46 | 40 |
| Particle size (at least 50% by weight of particles) (microns) | >500 | >500 | >500 | >600 |
| Viscosity (cp) | 13,760 | — | 20,100— | 24,770 |
| pH | 5.5–6.5 | 5.5–6.5 | 5.5–6.5 | 5.5–6.5 |
| Yield Point (dynes/sq. cm.) | 10 | — | 14 | 18 |

Encapsulated Particles Pre-mix Preparation:
1. Dissolve hexameta polyphosphate in 19 times as much water while stirring.
2. Dissolve gelatin in remaining water and heat to 50°–60° C. while stirring in agitated tank.
3. Heat lipophilic moisturizing agent to 50°–60° C.
4. Add hot lipophilic moisturizing agent at 50°–60° C. to gelatin-water solution at 50°–60° C.
5. Adjust agitation (RPM) to obtain desired particles size.
6. Add polyphosphate-water solution to gelatin-water-lipophilic moisturizing agent dispersion.
7. Add glacial acetic acid drop-wise until pH ranges from 3.8 to 5.0.
8. Cool particle mixture while stirring prior to incorporation of encapsulated particles into liquid personal cleansing matrix.

Incorporation of Encapsulated Particles into Personal Cleansing Matrix

The encapsulated lipophilic skin moisturizing agent particles are mixed into the personal cleansing matrix using a Kenics Static Mixer with a 1.5 inch diameter and 12 elements. The flow rate is adjusted until the desired % nonspherical particles is obtained (highly dependent on rheology).

What is claimed is:
1. A liquid personal cleansing composition comprising:
   a) a moisturizing phase comprising from about 1% to about 30% by weight of the composition of a lipophilic skin moisturizing agent; said agent comprised of droplets having a particle size distribution such that at least about 10% by weight of the droplets have a diameter of greater than about 500 microns; and b) an aqueous cleansing phase comprising i) from about 0.1% to about 10% by weight of the composition of a stabilizer, ii) from about 5% to about 30% by weight of the composition of a lathering surfactant, and iii) water.

2. A liquid personal cleansing composition according to claim 1 wherein the liquid personal cleansing emulsion composition has a Deposition Value of at least about 10 micrograms/square centimeter.

3. A liquid personal cleansing composition according to claim 2 wherein the lipophilic skin moisturizing agent has a consistency ranging from about 5 to about 5,000 poise and a shear index ranging from about 0.1 to about 0.9.

4. A liquid personal cleansing composition according to claim 3 wherein the lipophilic skin moisturizing agent is comprised of droplets having a particle size distribution such that at least about 50% by weight of the droplets have a diameter greater than about 500 microns.

5. A liquid personal cleansing composition according to claim 4 wherein the stabilizer is a crystalline, hydroxyl-containing stabilizer selected from the group consisting of:

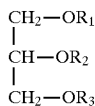   (i)

wherein

$R_2$ is $R_1$ or H
$R_3$ is $R_1$ or H
$R_4$ is $C_{0-20}$ Alkyl
$R_5$ is $C_{0-20}$ Alkyl,
$R_6$ is $C_{0-20}$ Alkyl
$R_4+R_5+R_6=C_{10-22}$
and wherein $1<x+y<4$;

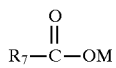   (ii)

wherein
$R_7$ is $-R_4(CHOH)_xR_5(CHOH)_yR_6$
M is $Na^+$, $K^+$ or $Mg^{++}$, or H; and
iii) mixtures thereof.

6. A liquid personal cleansing composition according to claim 5 wherein the viscosity of the liquid personal cleansing composition ranges from about 2,000 centipoise to about 100,000 centipoise.

7. A liquid personal cleansing emulsion composition according to claim 6 wherein the lathering surfactant comprises an anionic surfactant.

8. A liquid personal cleansing emulsion composition according to claim 7 wherein at least about 50% by weight of the droplets comprising the lipophilic skin conditioning agent have a diameter of greater than about 550 microns.

9. A liquid personal cleansing emulsion composition according to claim 8 which comprise from about 40% to about 65% water.

10. A liquid personal cleansing composition according to claim 9 which comprises from about 0.25% to about 8% of a stabilizer.

11. A liquid personal cleansing composition according to claim 10 which contains from about 5% to about 25% of a lathering surfactant.

12. A liquid personal cleansing composition according to claim 11 which has a Deposition Value of at least about 30 micrograms/square centimeter.

13. A liquid personal cleansing composition according to claim 12 wherein at least about 80% by weight of the droplets comprising the lipophilic skin conditioning agent have a diameter of greater than about 550 microns.

14. A liquid personal cleansing composition according to claim 13 which comprises from about 5% to about 25% of the lipophilic skin moisturizing agent.

15. A liquid personal cleansing composition according to claim 14 which has a yield point value ranging from about 5 to about 90 dynes/sq. cm.

16. A liquid personal cleansing composition according to claim 15 which has a viscosity ranging from about 10,000 centopoise to about 40,000 centipoise.

17. A liquid personal cleansing composition comprising:

a) a moisturizing phase comprising from about 1% to about 30% by weight of the composition of a lipophilic skin moisturizing agent; said agent comprised of droplets having a particle size distribution such that at least about 10% by weight of the droplets have a diameter of greater than about 500 microns; and b) an aqueous cleansing phase comprising i) from about 0.1% to about 10% by weight of the composition of a stabilizer, ii) from about 5% to about 30% by weight of the composition of a lathering surfactant, and iii) water;

wherein said personal cleansing composition is prepared by mixing together said moisturizing phase and said aqueous cleansing phase.

* * * * *